US00PP21575P3

(12) United States Plant Patent
Kitamura et al.

(10) Patent No.: US PP21,575 P3
(45) Date of Patent: Dec. 14, 2010

(54) MUSHROOM PLANT NAMED 'GRIFON 120'

(50) Latin Name: *Grifola frondosa*
Varietal Denomination: Grifon 120

(75) Inventors: Maki Kitamura, Nagano (JP); Eriko Kurashima, Nagano (JP)

(73) Assignee: Hokuto Corporation, Nagano-Ken (JP)

( * ) Notice: Subject to any disclaimer, the term of this patent is extended or adjusted under 35 U.S.C. 154(b) by 49 days.

(21) Appl. No.: 12/222,952

(22) Filed: Aug. 20, 2008

(65) Prior Publication Data

US 2009/0055986 P1 Feb. 26, 2009

(30) Foreign Application Priority Data

Aug. 21, 2007 (JP) ..... 21346

(51) Int. Cl.
*A01H 5/00* (2006.01)

(52) U.S. Cl. ..... Plt./394

(58) Field of Classification Search ..... Plt./394
See application file for complete search history.

*Primary Examiner*—Kent L Bell
(74) *Attorney, Agent, or Firm*—Wenderoth, Lind & Ponack L.L.P

(57) ABSTRACT

A new and distinct variety of mushroom, named 'Grifon 120', is described, which mushroom is characterized by its cap with thick flesh and delicious-looking whitish undersurface, good qualitative character and appearance, good keeping quality and storage life and delicious tasting. The mushroom can be cultivated by gathering and repeated breeding of fungal strains having dominant traits and is exquisite in stability, reproducibility and uniformity when being produced.

8 Drawing Sheets

Latin name: *Grifola frondosa* (Fr.) S.F. Gray
Varietal denomination: 'Grifon 120'.

FIELD OF THE INVENTION

The present invention relates to a new and distinct cultivar of mushroom plant, named 'Grifon 120', of the species *Grifola frondosa.*

BACKGROUND OF THE INVENTION

*Grifola frondosa*, also known as Maitake, has been richly cultivated artificially in Japan for a long time and known familiarly as healthy ingredient. In recent years, the demand of Maitake comestible as supplement is increasing because the hot water extract from Maitake is considered as effective against cancer. So, growth in demand of Maitake in the form of fresh food is expected. Ease of cultivation and improvement in productivity of the mushroom are required for expedite sales.

It is critical element that the appearance, taste, preservative quality and tempting color of *Grifola frondosa* broth to be accepted in a market. About the broth, it is pointed out that *Grifola frondosa* broth is deep in color with variety.

On the other hand, *Grifola frondosa* had been cultivated based on wild mushroom tissue disaggregation. However, it has been so far difficult to control the postplanting environment for *Grifola frondosa* artificially, and mass-produce the mushroom. Thus, a new mushroom species was bred by cross-breeding techniques. For example, there has been a new variety of *Grifola frondosa* named 'Hokuto NT-100' as disclosed in U.S. Plant Pat. 17,984, which features ease of cultivating, fine flavor and improved storage stability. However, the aforementioned 'Hokuto NT-100' still has room for improvement in coloration and keeping quality.

SUMMARY OF THE INVENTION

In view of the foregoing, the present invention provides a new and distinct variety of mushroom characterized particularly by its cap with thick flesh and delicious-looking whitish undersurface, good qualitative character and appearance, good keeping quality and storage life and delicious tasting, which can be cultivated by gathering and repeated breeding of fungal strains having dominant traits and is exquisite in stability, reproducibility and uniformity when being produced. This novel and distinct variety of mushroom is identified as 'Grifon 120'.

BRIEF DESCRIPTION OF THE FIGURES

The accompanying photographic drawings illustrate the new variety, with the color being as nearly true as is possible with color illustrations of this type.

DETAILED DESCRIPTION OF THE INVENTION

Figure 1A:
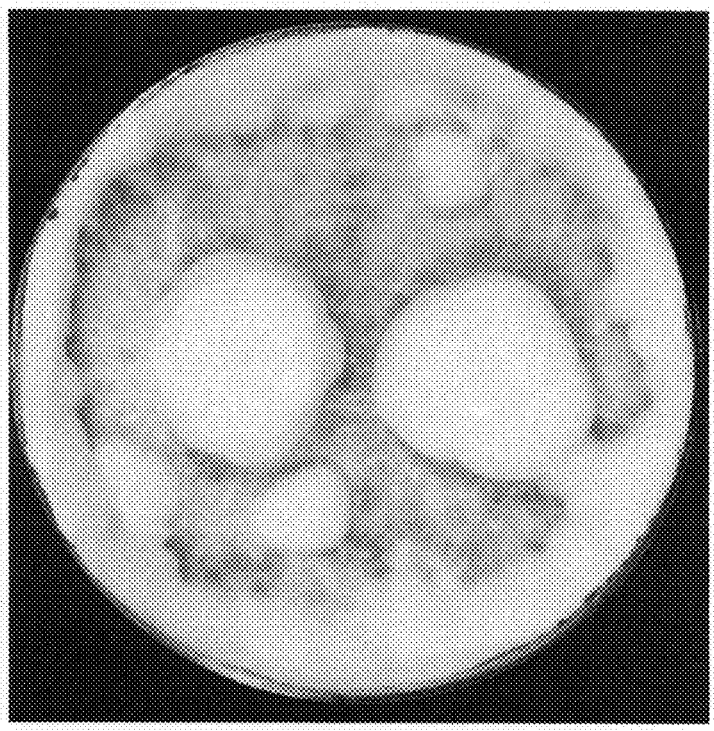
FIGS. 1(A) and 1(B) are photographs showing top and bottom of dual culture in which a pair of 'Grifon 120' strains of the invention are placed alongside.
Figure 1B:
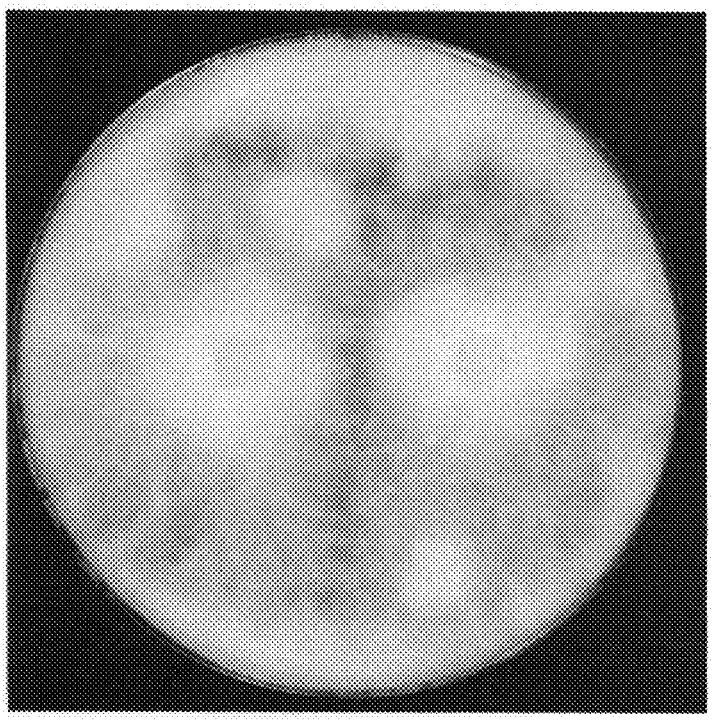
Figure 2A:
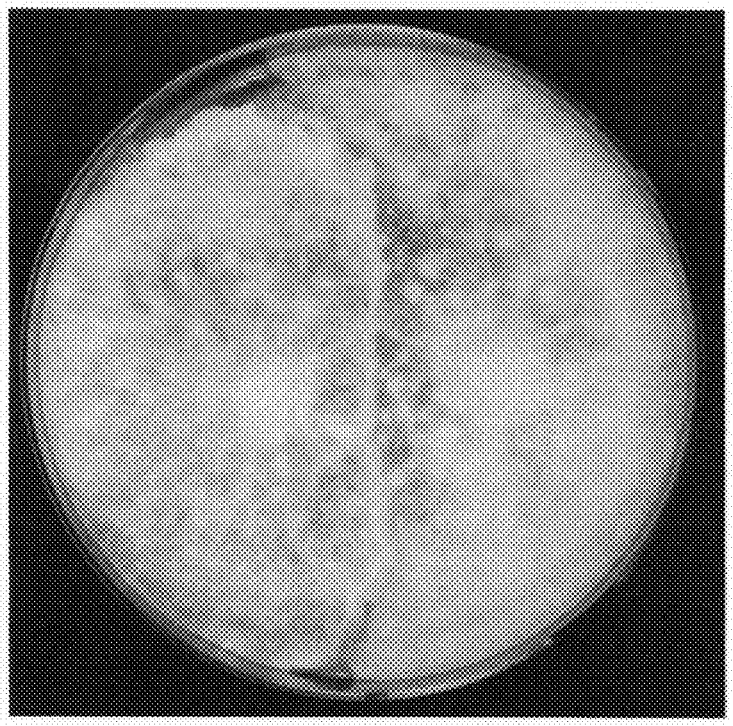
FIGS. 2(A) and 2(B) are photographs showing top and bottom of dual culture in which 'Grifon 120' strain and parent strain 'HOKUTO NT-100' are placed alongside.
Figure 2B:
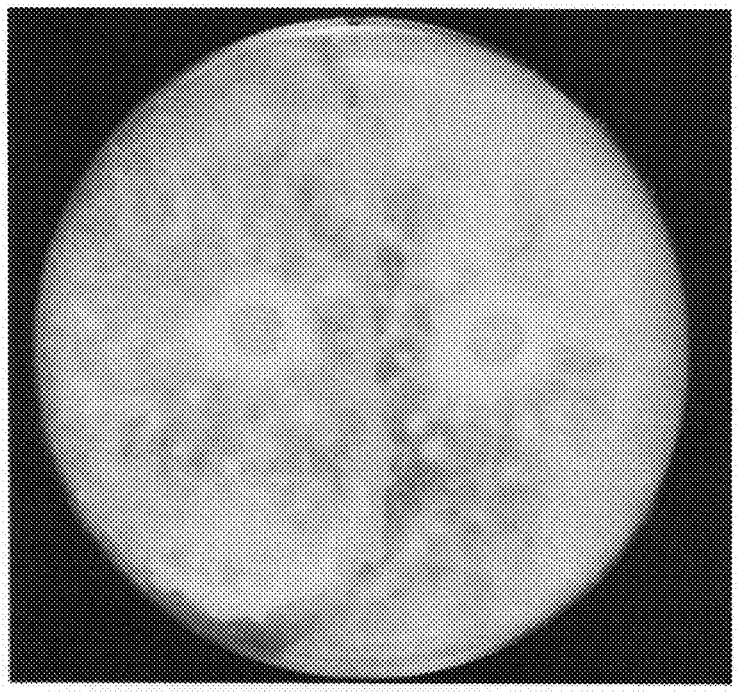
Figure 3A:
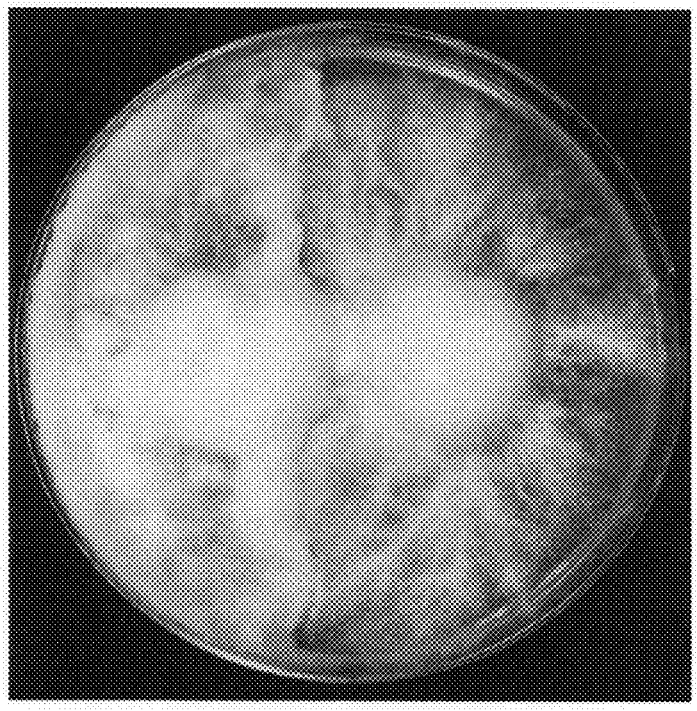
FIGS. 3(A) and 3(B) are photographs showing top and bottom of dual culture in which 'Grifon 120' strain and parent strain 'HOKUTO MY-95' are placed alongside.
Figure 3B:
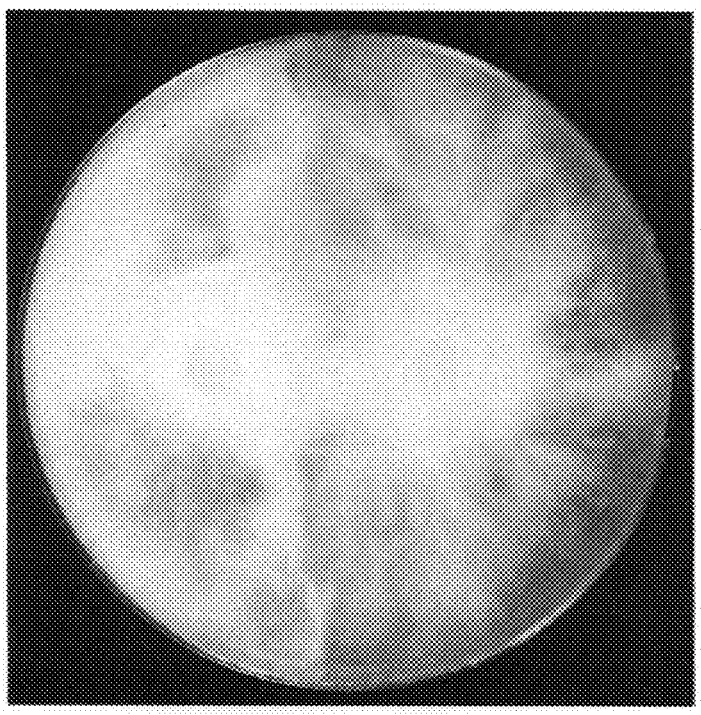
Figure 4A:
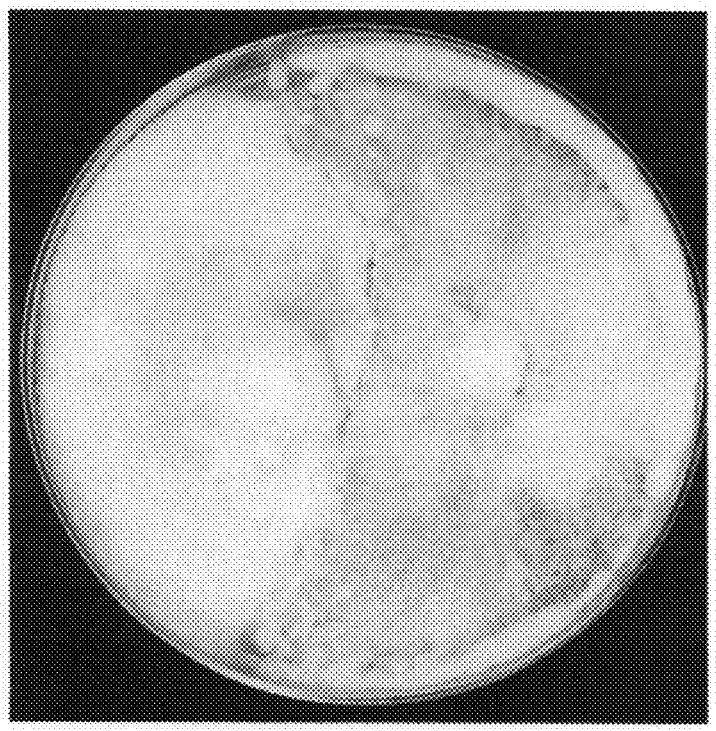
FIGS. 4(A) and 4(B) are photographs showing top and bottom of dual culture in which 'Grifon 120' strain and control strain 'MH182011' are placed alongside.
Figure 4B:
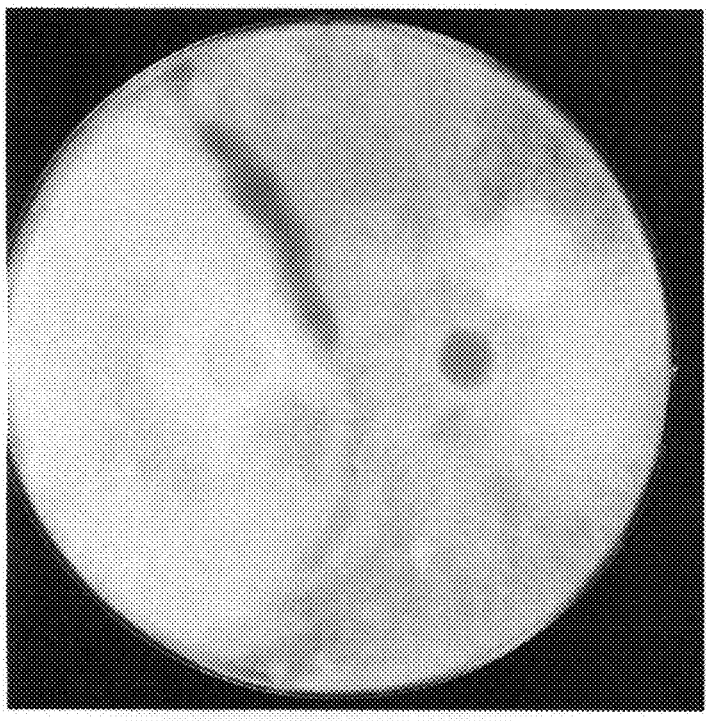
Figure 5:
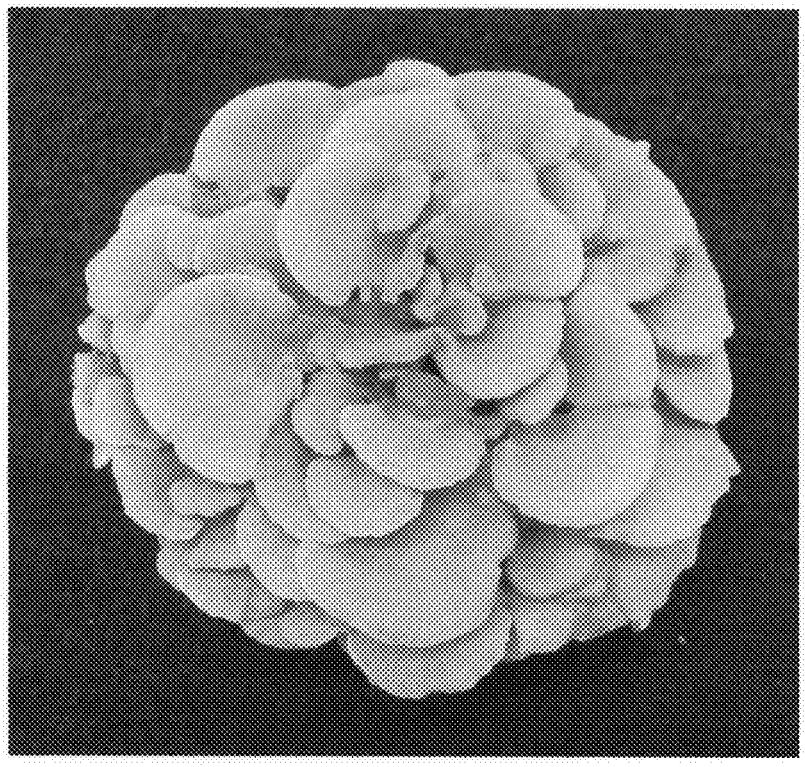
FIG. 5 is a photograph showing the mazaedium of 'Grifon 120' of the invention.
Figure 6:
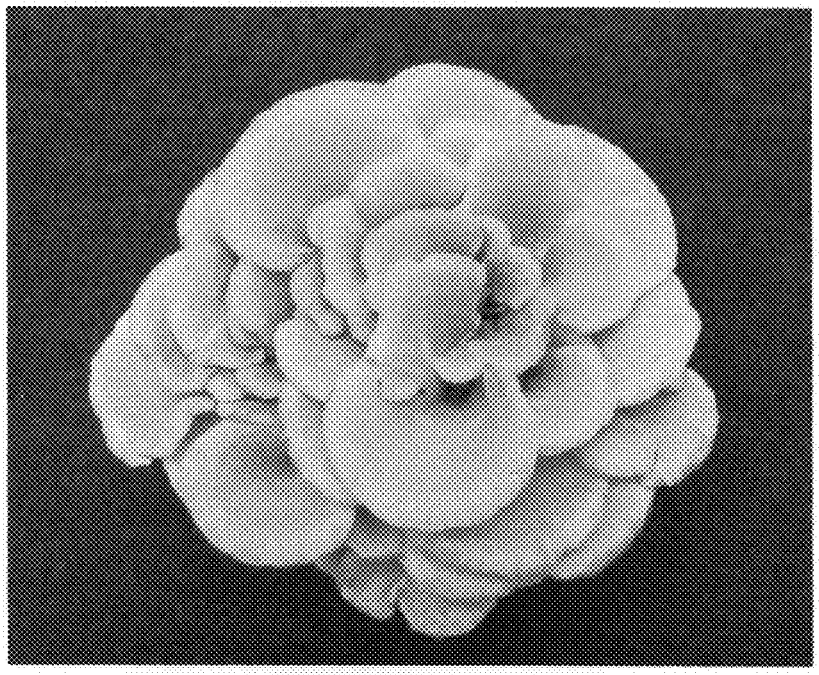
FIG. 6 is a photograph showing the mazaedium of the parent strain 'HOKUTO NT-100'.
Figure 7:
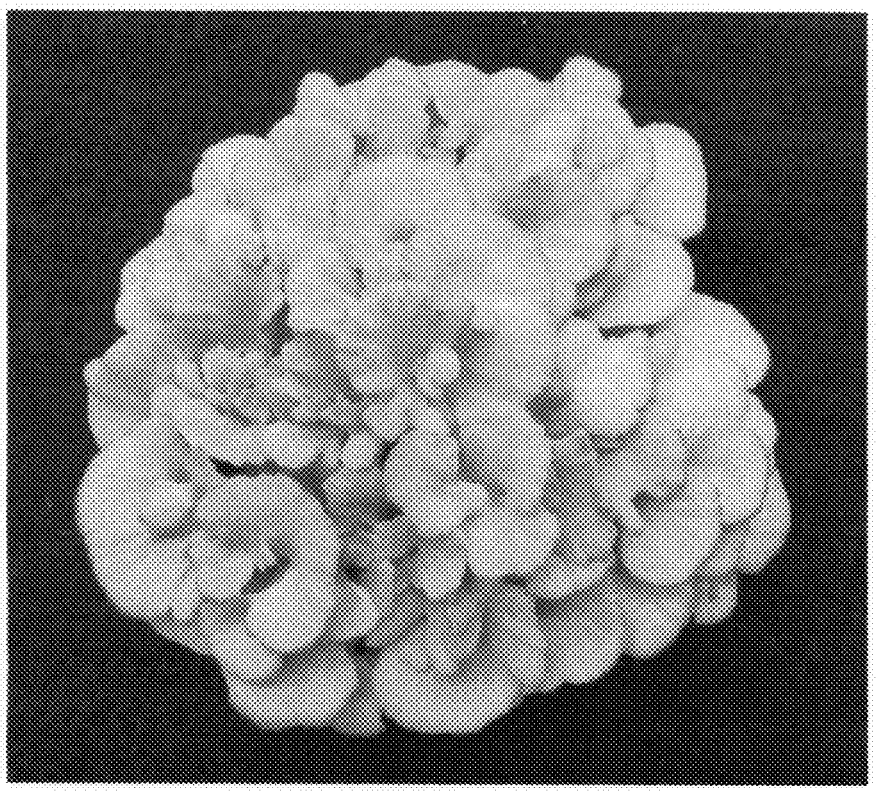
FIG. 7 is a photograph showing the mazaedium of the parent strain 'HOKUTO MY-95'.
Figure 8:
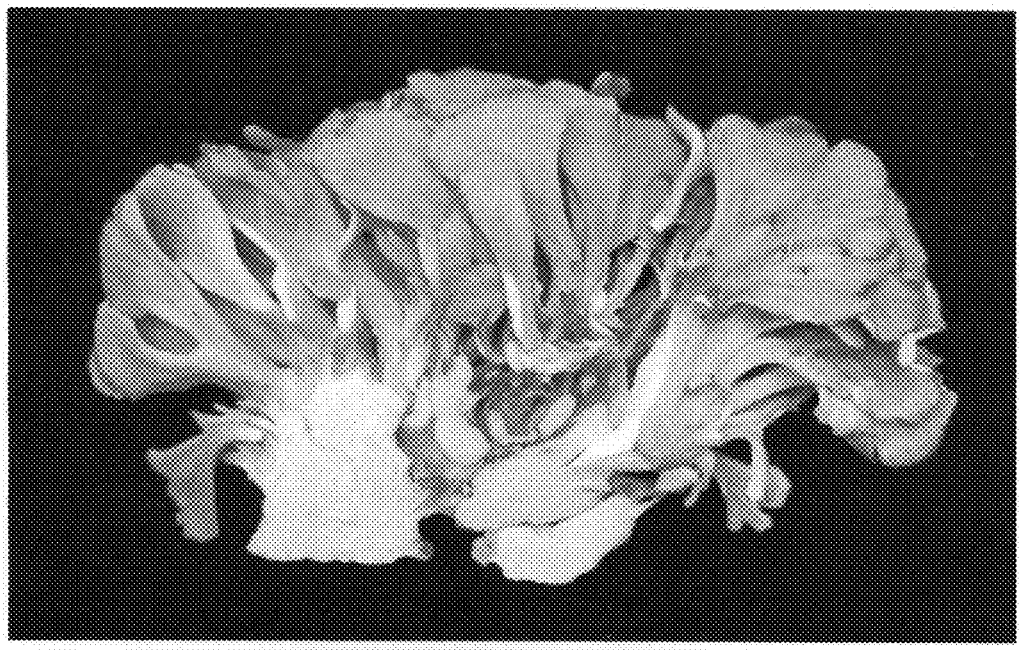
FIG. 8 is a photograph showing the mazaedium of the control strain 'MH182011'.
Figure 9A:
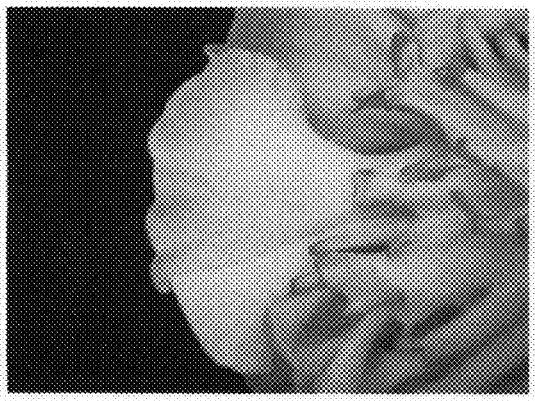
FIGS. 9(A) through 9(D) are photographs showing the cap gills of the strains 'Grifon 120' (FIG. 9(A)), 'HOKUTO NT-100' (FIG. 9(B)), 'HOKUTO MY-95' (FIG. 9(C)) and 'MH182011' (FIG. 9(D)).
Figure 9B:
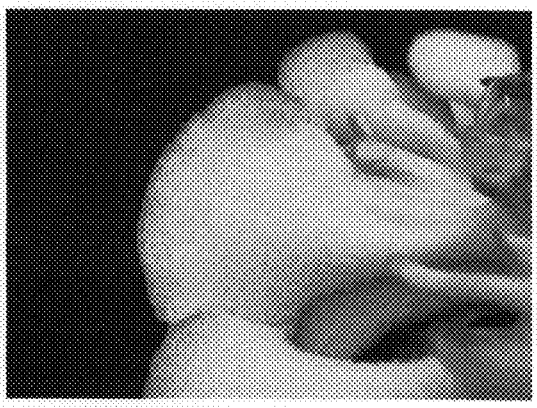
Figure 9C:
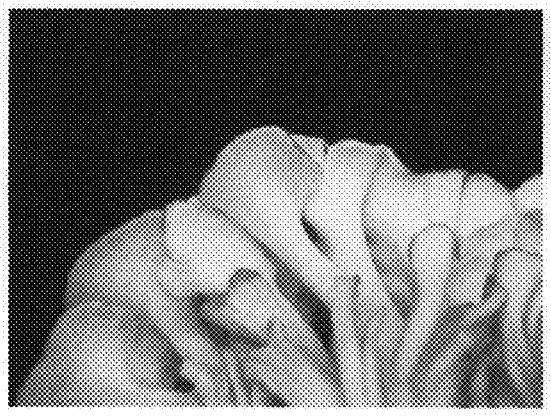
Figure 9D:
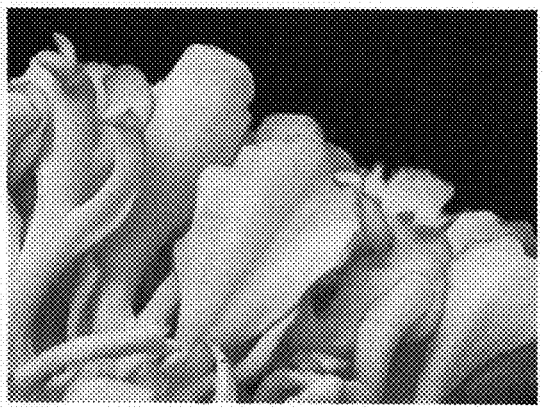

The present invention relates to a new and distinct variety of mushroom, Maitake named 'Grifon 120', characterized particularly by its cap with thick flesh and delicious-looking whitish undersurface, good qualitative character and appearance, good keeping quality and storage life and delicious tasting.

The Maitake 'Grifon 120' of the invention is cultivated by bringing indigenous fungal strains and commonly-available fungal strains. An example of the cultivation of the Maitake 'Grifon 120' will be described hereinafter. In this cultivation, the following fungal strains similar to 'Grifon 120' in variety were used as parent varieties.

1. Fungal strain: Maitake named 'Hokuto MY-95' registered as a new plant variety under Reg. No. 8624 by the Ministry of Agriculture, Forestry and Fisheries of Japan on Dec. 22, 2000.
2. Fungal strain: Maitake named 'Hokuto NT-100' registered as a new plant variety under Reg. No. 14031 by the Ministry of Agriculture, Forestry and Fisheries of Japan on Mar. 9, 2006. This strain has been patented under U.S. Plant Pat. 17,984.

The aforementioned fungal strains were all developed and duly registered as new variety of mushroom by the assignee's company in Japan.

The record of actually bringing the 'Grifon 120' of the invention into cultivation is described below. The cultivating record is of help to understand the cultivation method of 'Grifon 120' of the invention to recreate the invention.

1. (Jan. 1993): 'Hokuto MY-95' was cultivated.
2. (Jan. 2002): 'Hokuto NT-100' was cultivated.
3. (Sep. 2002): Fungal hyphae was separated from Maitake (*Grifola frondosa*) gathered from the wild in Yamagata, Japan, to obtain a fungal strain named 'MH182099'.
4. (Feb. 2004): From fungal strains obtained by crossing 'Hokuto MY-95' and 'MH182099', there was sorted out a fungal strain having a cap with whitish undersurface as intended, which was named 'MH182188'.
5. (Aug. 2006): A quality fungal strain (Specimen Maitake #G060383) conformable to the breeding objective was obtained by crossing 'Hokuto NT-100' and 'MH182188'. As the result of repeating the cultivation experiment, identification and productive stability and uniformity of the obtained Maitake #G060383 could be confirmed, thus to name the Maitake 'Grifon 120'.
6. (Aug. 2007) An application for plant variety registration for 'Grifon 120' was filed with the Ministry of Agriculture, Forestry and Fisheries of Japan.

(1) Comparison of Maitake 'Grifon 120' with existing varieties in dual culture:

For identifying specific characteristics of the 'Grifon 120', dual culture using commercially available cultivars as parent controls was performed to investigate idiosyncrasy of fungi showing a reluctance to touch others.

The investigation was conducted by seeding the fungal strains of 'Grifon 120' and other control fungi upon a potato dextrose agar medium in such a manner that the fungal strains of 'Grifon 120' are confronted with the control fungi at intervals of 3 cm, cultivating the strains at 25 degrees C. for 28 days, and then, determining whether the strains show the reluctance to touch others.

The fungal strains used in the comparative experiments are as follows:

1. 'Grifon 120': (Maitake #G060383) Strain according to the invention.
2. 'Hokuto NT-100': Parent variety similar to 'Grifon 120', as described above.
3. 'Hokuto MY-95': Similar variety to 'Grifon 120', as described above.
4. 'MH182011': Common cultivar available commercially in Japan, which was used as a control strain.

In the result, the comparative experiments thus performed revealed that 'Grifon 120' of the invention shows the reluctance to touch all the other strains (see Table 1 and FIGS. 1 to 4). Consequently, it is evident from the experiments that 'Grifon 120' is a new variety of *Grifola frondosa*.

TABLE 1

| Results of Dual Culture | | | |
|---|---|---|---|
| | Similar Variety | | Commercial Strain |
| | NT-100 | MY-95 | MH082011 |
| 'Grifon 120' | + | + | + |

* Strains 'Grifon 120' have no reluctance to touch each other.

(2) Cultural characteristics of 'Grifon 120':

1. 'Grifon 120' cultivated on the potato dextrose agar medium has the following characteristics. The mycelial color is white, shape of the surface of the colony is smooth, shape of colony edge is irregular, colony thickness is thick, and density of hyphae is sparse (see Tables 2-4).
2. The optimal temperature for hyphal growth was approximately 26 degrees C. (see Tables 2-4).

TABLE 2

| Characteristics | Characteristic Code of Filed Variety | | | | | | | | |
|---|---|---|---|---|---|---|---|---|---|
| | 01 | 02 | 03 | 04 | 05 | 06 | 07 | 08 | 09 |
| Genetic | – | | | | | | | | + |
| Dual Culture Reluctance-to-touch | | | | | | | | | |
| Physiology | | | | | | | | | |
| Mycelial Growth | | | | | | | | | |
| Optimum Temperature (° C.) | 20 | 22 | 24 | 26 | 28 | 30 | | | |
| Growth Rate | | | | | | | | | |
| 10° C. | | | | | | | | | |
| 15° C. | | | | | | | | | |

TABLE 2-continued

| | | | |
|---|---|---|---|
| 20° C. | | | |
| 25° C. | | | |
| 30° C. | | | |
| 35° C. | | | |
| Mycelial Color | White | | Other |
| Shape of Surface of Colony | Smooth | Laugh | Other |

| Characteristics | Note (Data) | Parent Variety 'Hokuto NT-100' | Parent Variety 'Hokuto MY-95' | Commercial Strain 'MH082011' |
|---|---|---|---|---|
| Genetic Dual Culture Reluctance-to-touch | — | 09 | 09 | 09 |
| Physiology Mycelial Growth Optimum Temperature (° C.) | 04 | 04 | 05 | 05 |
| Growth Rate | (mm/day) | (mm/day) | (mm/day) | (mm/day) |
| 10° C. | 1.2 | 0.4 | 0.6 | 0.8 |
| 15° C. | 1.5 | 1.4 | 1.7 | 1.8 |
| 20° C. | 2.4 | 2.3 | 2.6 | 2.5 |
| 25° C. | 2.7 | 3.1 | 2.9 | 2.9 |
| 30° C. | 2.0 | 1.9 | 2.9 | 2.7 |
| 35° C. | 0.0 | 0.0 | 0.0 | 0.0 |
| Mycelial Color | 01 | 01 | 01 | 01 |
| Shape of Surface of Colony | 01 | 01 | 01 | 01 |

TABLE 3

| Characteristics | Characteristic Code of Filed Variety 01 | 02 | 03 | 04 | 05 | 06 |
|---|---|---|---|---|---|---|
| Shape of Colony Edge | Irregular | | | | | |
| Colony Thickness | | | Thin | | Medium | |
| Hypha Density | | | Sparse | | Medium | |
| Cultivation Characteristics | | | | | | |
| Capsule Formation | | | Little | | Medium | |
| Capsule Coloration | None | | | | | |
| Length of Time until fruit body formation at optimal temperature (Days) | <30 | 31~40 | 41~50 | 51~60 | 61~70 | >70 |
| Optimal Development Temperature (° C.) | <15 | 15~20 | 20~25 | >25 | | |
| Optimal Fruit Body Growth Temperature (° C.) | <18 | 18~21 | >21 | | | |

TABLE 3-continued

| | | | | | | |
|---|---|---|---|---|---|---|
| Temperature (° C.) | | | | | | |
| Budding period (Natural Cultivation) | | | Early | | Normal | |
| Yield (g/bottle) | 400 | 450 | 500 | 550 | 600 | 650 |

| Characteristics | Characteristic Code of Filed Variety 07 | 08 | 09 | Note (Data) |
|---|---|---|---|---|
| Shape of Colony Edge | | | Regular | 01 |
| Colony Thickness | Thick | | | 07 |
| Hypha Density | Dense | | | 03 |
| Cultivation Characteristics | | | | |
| Capsule Formation | Much | | | 05 |
| Capsule Coloration | | | ○ | 01 |
| Length of Time until fruit body formation at optimal temperature (Days) | | | | 03 |
| Optimal Development Temperature (° C.) | | | | 03 |
| Optimal Fruit Body Growth Temperature (° C.) | | | | 02 |
| Budding period (Natural Cultivation) | Late | | | 05 |
| Yield (g/bottle) | 700 | 750 | 800 | 07 |

| Characteristics | Parent Variety 'HOKUTO NT-100' | Parent Variety 'HOKUTO MY-95' | Commercial Strain 'MH082011' |
|---|---|---|---|
| Shape of Colony Edge | 01 | 01 | 09 |
| Colony Thickness | 05 | 05 | 03 |
| Hypha Density | 03 | 03 | 03 |
| Cultivation Characteristics | | | |
| Capsule Formation | 05 | 05 | 05 |
| Capsule Coloration | 01 | 01 | 09 |
| Length of Time until fruit body formation at optimal temperature (Days) | 03 | 03 | 06 |
| Optimal Development Temperature (° C.) | 03 | 03 | 02 |
| Optimal Fruit Body Growth Temperature (° C.) | 02 | 02 | 01 |

TABLE 3-continued

| | | | |
|---|---|---|---|
| Budding period (Natural Cultivation) | 05 | 05 | 05 |
| Yield (g/bottle) | 05 | 07 | 01 |

TABLE 4

| Characteristics | Characteristic Code of Filed Variety | | | | | | | |
|---|---|---|---|---|---|---|---|---|
| | 01 | 02 | 03 | 04 | 05 | 06 | 07 | 08 |
| Morphology | | | | | | | | |
| Cap Size | | | Small | | Medium | | Large | |
| Thickness | | | Thin | | Medium | | Thick | |
| Notch | None | | | | | | | |
| Cross sectional shape | 1 | 2 | 3 | | | | | |
| Face color | W | G-W | D-G | B | D-B | | | |
| Annulus | 1 | 2 | 3 | 4 | | | | |
| Hair | | | Few | | Medium | | Many | |
| Shape of Tube Face | 1 | 2 | 3 | 4 | | | | |
| Unevenness of cross sectional the tip of tube | None | | | | | | | |
| Tube Position | 1 | 2 | 3 | | | | | |
| Stipe Shape | 1 | 2 | 3 | | | | | |

| Characteristics | Characteristic Code of Filed Variety 09 | Note (Data) | Parent Variety 'Hokuto NT-100' | Parent Variety 'Hokuto 'MY-95' |
|---|---|---|---|---|
| Morphology | | | | |
| Cap Size | | 07 | 07 | 05 |
| Thickness | | 05 | 05 | 05 |
| Notch | ○ | 01 | 01 | 01 |
| Cross sectional shape | | 02 | 02 | 02 |
| Face color | Other | Royal Horticultural Society: RHS Color Chart | | |
| | | Grey-brown (199a) | Grey-brown (199b) | Grey-brown (n199c) |
| Annulus | Other | 03 | 04 | 04 |
| Hair | | 03 | 03 | 03 |
| Shape of Tube Face | Other | 01 | 01 | 01 |
| Unevenness of cross sectional the tip of tube | Present | 01 | 01 | 01 |
| Tube Position | Other | 03 | 03 | 03 |
| Stipe Shape | Other | 02 | 02 | 03 |

| Characteristics | Commercial Strain 'MH082011' |
|---|---|
| Morphology | |
| Cap Size | 07 |
| Thickness | 05 |
| Notch | 09 |
| Cross sectional shape | 02 |

TABLE 4-continued

| | |
|---|---|
| Face color | Royal Horticultural Society: RHS Color Chart Grey-brown (199c) |
| Annulus | 02 |
| Hair | 03 |
| Shape of Tube Face | 01 |
| Unevenness of cross sectional the tip of tube | 09 |
| Tube Position | 03 |
| Stipe Shape | 01 |

"Commercial Strain" means the commercially available strains used as control strains in contraposition to the instant mushrooms.

"Royal Horticultural Society (R.H.S. Color Chart)" The color codes described in the foregoing Tables matched with the R.H.S. Color Chart prescribed by Royal Horticultural Society, England. Namely, the code numbers 199a, 199b and 199c in parentheses in the row "Face Color"in Table 4 corresponds to the R.H.S. Color Chart.

"Characteristic Code of Filed Variety" The characteristics (traits) of the instant mushrooms 'Grifon 120' are rated on a scale of one (01) to nine (09) in this column of the tables. The aspects relevant to the traits of the mushrooms correspond to the scale numbers.

"Note (Data)" The characteristics of the instant mushrooms 'Grifon 120' are denoted in this column of the tables and correspond to the numbers 01-09⁻, i.e. 'Characteristic Codes of Filed Variety'.

"Parent Variety" The parent varieties of the instant mushrooms 'Grifon 120' are denoted in this column of the tables. Incidentally, the parents of 'Grifon 120' are 'HOKUTO MY-95', 'HOKUTO NT-100', 'MH182099' and 'MH182188' as described in the specification.

(3) Morphological characteristics of 'Grifon 120':

| | CONFIGURATION | RHS COLOR CODE |
|---|---|---|
| PILEUS | Shape: Fan-like form (sector)<br>Lateral Diameter: 40.13 mm<br>(Standard Deviation: 16.04; n = 142)<br>Thickness: 2.57 mm<br>(Standard Deviation: 0.58; n = 142) | 199a<br>Gray-brown |
| Gill | None | |
| Stipe | Slender | |

CULTIVATION METHOD (Culture Vessel) Twenty polypropylene culture bags with a ventilating filter, which is formed in a square and has the dimensions of 8500 to 9000 cc in volume, 200×120 mm in bore diameter, and 460 mm in height, were prepared for cultivation of the fungal strains. The cultivation of the fungal strains was performed twice, using the ten culture bags each time.

(Culture Medium) Culture media composed of sawdust of broadleaf tree, especially beechwood, and corn bran was used. Each culture bag was filled with 2.5 kg of the culture medium at a mixture ratio of 1 kg of sawdust, 0.5 kg of corn bran and 2.1 kg of water (ratio by weight) and sterilized by autoclaving.

(Seed Fungus) Seed fungus composed of sawdust was used. About 25 cc of seed fungus was inoculated upon each culture medium.

(Cultivation) Cultivation was performed for 40 to 70 days at a temperature of 20 to 25 degrees C., at a humidity of 60% to 70%, and at an illumination intensity of 200 to 500 lux. The time when primordium of the objective fungal strain is formed and colored was determined to be an ending time period of cultivation.

(Strain Growth) After the cultivation, the growing condition of the strains was shifted to the condition of a temperature of 15 to 20 degrees C., a humidity of 80% to 95% and an illumination intensity of 500 to 1500 lux to make mazaedia of the strains grow. The time when pores appear in the cap gill was determined to be harvesttime.

RESULT OF CULTIVATION

The cultural experiment clarifies the differences between 'Grifon 120' of the invention and the control fungal strains including the most similar strains, as shown in Tables 2 to 4 above. The mazaedia of the strains are shown in FIG. 4 through FIG. 8.

(4) Morphological characteristics of the cap gill of Grifon120

Comparison was observed about a pore and gill color of 'Grifon 120' and similar varieties. The results are shown in the picture of the accompanying drawing.

The cap gill is more white than that of the similar species 'HOKUTO NT-100' similar to 'Grifon 120', and slightly colored. The pores in the gill were also made slow grow beyond recognition (FIG. 9).

(5) Features of the broth decocted from 'Grifon 120' (Table 5)

Figure 10:
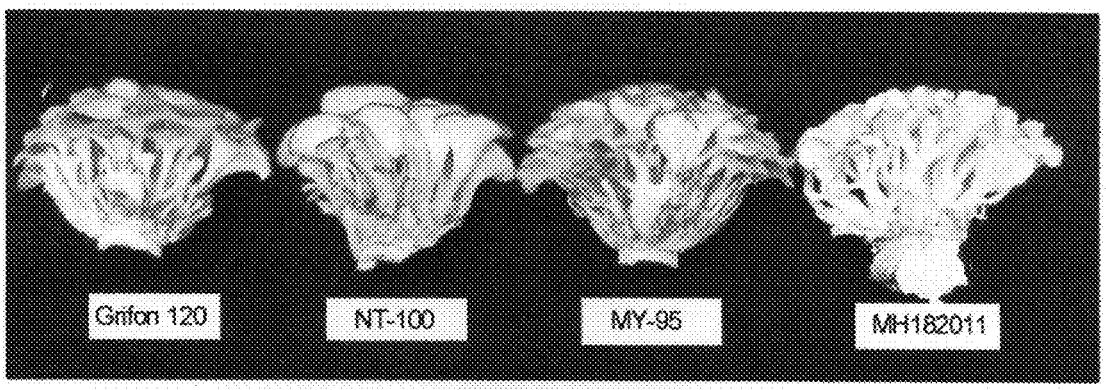
FIG. 10 is a comparative photograph showing the strains 'Grifon 120', 'HOKUTO NT-100', 'HOKUTO MY-95' and 'MH182011' placed abreast in order.
Figure 11:
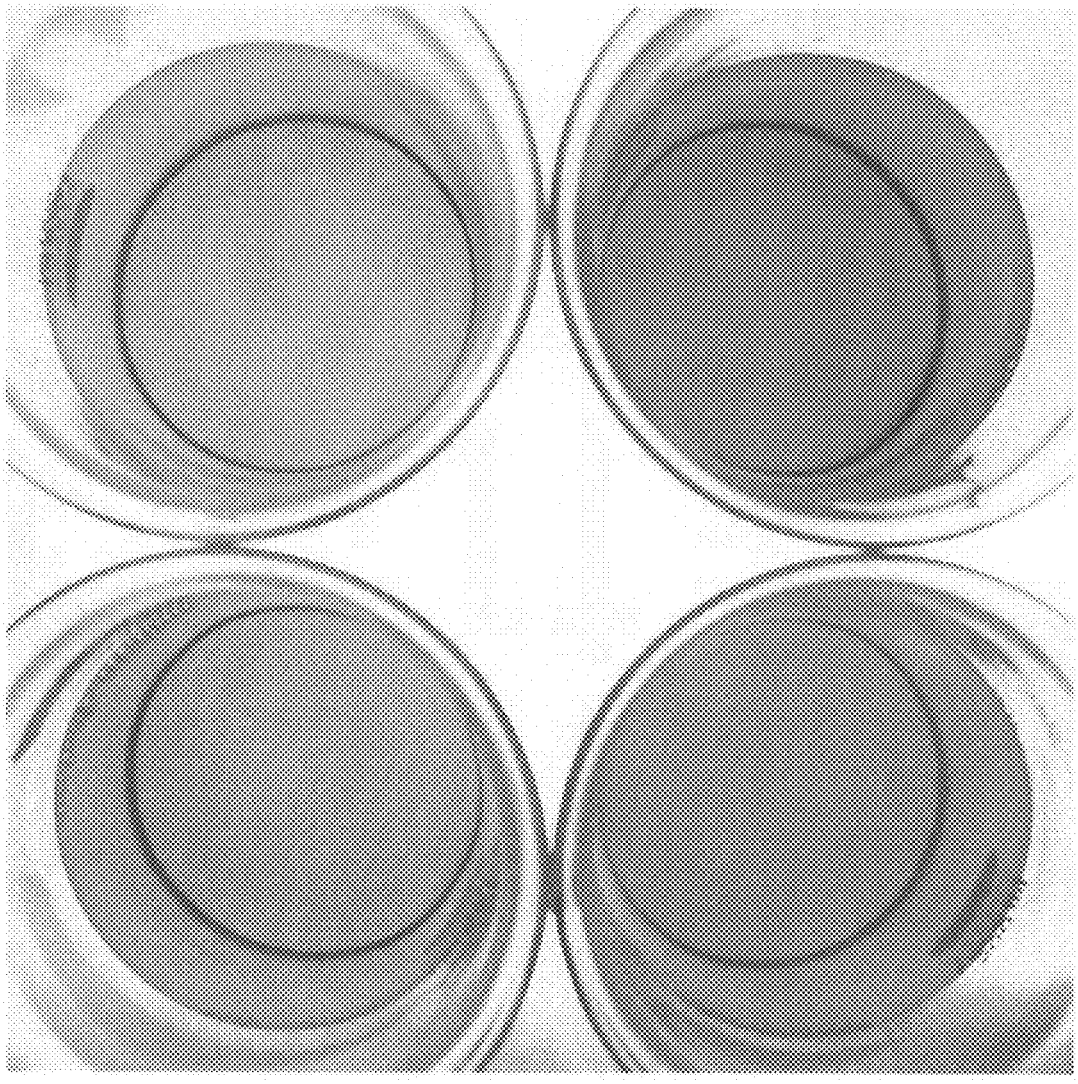
FIG. 11 is a comparative photograph showing four cups of broth of strains 'Grifon 120' (upper left), 'HOKUTO NT-100' (upper right), 'HOKUTO MY-95' (lower left) and 'MH182011' (lower right).

A comparison of broth between 'Grifon 120' of the invention and the similar varieties was drawn to evaluate 'Grifon 120'. The broth of the strains in the experiment was obtained by boiling hot water containing 100 grams of the strain mazaedium over high heat for 30 seconds, further boiling the hot water for 30 seconds over gentle heat, and then bringing out the mazaedium from the hot water. The broths obtained resultantly from the comparative investigation performed for the strains were measured in concentration by comparison. (FIG. 10)

The result was that 'Grifon 120' was weaker in broth concentration than the commercial varieties of strains, but substantially equal to the similar variety 'NT-100'.

TABLE 5

Comparison of absorbance of broths
Absorption wavelength 437 nm

| | Fungal strain | | | |
|---|---|---|---|---|
| | 'Grifon 120' | 'HOKUTO NT-100' | 'HOKUTO MY-95' | 'MH182011' |
| Absorbance | 0.214 | 0.218 | 0.253 | 0.263 |

(6) Eating-quality test of 'Grifon 120' (Table 6)

The eating-quality of 'Grifon 120' of the invention was compared with 'Hokuto NT-100'. 'Grifon 120' is a strain improved from the parent variety NT-100 to enhance the cultural and eating quality thereof as described above. However, new varieties obtained by breeding do not always have the same flavor and texture. The strain does not always become tasteless even though the strain is made better in morphology. Thus, a taste test of the strains was also carried out.

The resultantly obtained fungi (mushrooms) were preserved in a common environment as would be for ordinary distribution. That is, the mushrooms were preserved at 3 degrees C. for 5 days after harvesting, at 30 degrees C. for two days, and further 15 degrees C. for three days. Then, on the tenth day after harvesting, a taste test was carried out.

The taste test was conducted by 64 monitors eating mushrooms, a questionnaire on the taste of the mushrooms was then carried out. The results of a questionnaire are shown in Table 6.

TABLE 6

Results of Taste Test

| | | Daintiness | | | | Firmness | | | Ranking | |
|---|---|---|---|---|---|---|---|---|---|---|
| | | A | B | C | E | G | N | E | D | E |
| 'NT-100' | (ppl) | 13 | 39 | 11 | 1 | 46 | 18 | 0 | 16 | 14 |
| | (%) | 20 | 61 | 17 | 2 | 72 | 28 | 0 | 25 | |
| 'Grifon 120' | (ppl) | 28 | 31 | 5 | 0 | 57 | 7 | 0 | 34 | 22 |
| | (%) | 44 | 48 | 8 | 0 | 89 | 11 | 0 | 53 | |

[Daintiness] A: Good taste B: Fair C: Bad taste E: No opinion
[Firmness] G: Crunchy N: Soft E: No opinion
[Ranking] D: Rated as "tasty" by comparison with others E: No opinion As will be appreciated from the results shown in Table 6, 'Grifon 120' of the invention is better in daintiness and firmness than the control varieties. 'Grifon 120' was chosen as "higher-ranking" by 53 percent of monitors while the control variety 'HOKUTO NT-100' was chosen by 25 percent of monitors. Thus, 'Grifon 120' of the invention should prove dainty to the consuming public.

CONCLUSION

The new variety 'Grifon 120' produced by breeding according to the invention is different in morphologic attribute from the similar variety 'HOKUTO NT-100' and superior to the control variety 'MH182011' in terms of morphology, broth denseness and eating quality.

What is claimed is:

1. A new and distinct variety of mushroom, substantially as described and illustrated herein.

* * * * *